United States Patent
Koulikov

(10) Patent No.: US 11,209,354 B2
(45) Date of Patent: Dec. 28, 2021

(54) LASER ABSORPTION SPECTROSCOPY ISOTOPIC GAS ANALYZER

(71) Applicant: Serguei Koulikov, Los Altos, CA (US)

(72) Inventor: Serguei Koulikov, Los Altos, CA (US)

(*) Notice: Subject to any disclaimer, the term of this patent is extended or adjusted under 35 U.S.C. 154(b) by 0 days.

(21) Appl. No.: 17/026,017

(22) Filed: Sep. 18, 2020

(65) Prior Publication Data

US 2021/0003503 A1 Jan. 7, 2021

Related U.S. Application Data

(63) Continuation of application No. 16/407,144, filed on May 8, 2019, now Pat. No. 10,830,694, which is a continuation of application No. 15/854,801, filed on Dec. 27, 2017, now Pat. No. 10,330,592.

(60) Provisional application No. 62/535,505, filed on Jul. 21, 2017.

(51) Int. Cl.
| | |
|---|---|
| *G01N 21/3504* | (2014.01) |
| *G01N 21/71* | (2006.01) |
| *G01N 33/15* | (2006.01) |
| *G01N 21/27* | (2006.01) |
| *G01N 21/31* | (2006.01) |
| *G01J 3/42* | (2006.01) |
| *G01N 21/39* | (2006.01) |
| *G01N 21/17* | (2006.01) |

(52) U.S. Cl.
CPC ............ *G01N 21/3504* (2013.01); *G01J 3/42* (2013.01); *G01N 21/27* (2013.01); *G01N 21/31* (2013.01); *G01N 21/39* (2013.01); *G01N 21/716* (2013.01); *G01N 33/15* (2013.01); *G01N 2021/1704* (2013.01); *G01N 2021/1748* (2013.01); *G01N 2021/399* (2013.01); *G01N 2201/0612* (2013.01)

(58) Field of Classification Search
CPC ...... G01N 21/716; G01N 21/31; G01N 21/39; G01N 21/3504; G01N 33/15; G01N 21/27; G01N 2201/0612; G01N 2021/1748; G01N 2021/399; G01N 2021/1704; G01N 21/00; G01N 21/1702; G01N 33/0004; G01J 3/42; G01J 3/10
See application file for complete search history.

(56) References Cited

U.S. PATENT DOCUMENTS

| | | | | |
|---|---|---|---|---|
| 8,665,442 B2 * | 3/2014 | Koulikov | ............... | G01N 21/59 356/437 |
| 8,681,336 B2 * | 3/2014 | Nickerson | ............... | G01N 33/24 356/437 |
| 8,823,923 B2 * | 9/2014 | Berman | ............... | G01N 21/031 356/39 |

(Continued)

FOREIGN PATENT DOCUMENTS

| | | | | |
|---|---|---|---|---|
| WO | WO-0113091 A2 * | 2/2001 | ............ | G01J 3/0232 |
| WO | WO-0204903 A1 * | 1/2002 | ............ | G01N 21/39 |

(Continued)

*Primary Examiner* — Mohamed K Amara

(57) ABSTRACT

The present invention provides systems and methods for measuring the isotope ratios of one or more trace gases based on optical absorption spectroscopy methods. The system includes an optical cavity containing a gas. The system also includes a laser optically coupled with the optical cavity, and a detector system for measuring absorption of laser light by the gas in the cavity.

15 Claims, 18 Drawing Sheets

(56) References Cited

U.S. PATENT DOCUMENTS

| | | | | |
|---|---|---|---|---|
| 8,982,352 B1* | 3/2015 | Hoffnagle | ................ | G01J 3/42 |
| | | | | 356/437 |
| 9,194,794 B2* | 11/2015 | Wilkins | ............. | G01N 21/3577 |
| 9,766,219 B2* | 9/2017 | Wapelhorst | ........ | G01N 33/0011 |
| 9,829,432 B2* | 11/2017 | Maekawa | ............ | G01N 21/05 |
| 9,874,513 B2* | 1/2018 | Schlueter | ............. | G01N 21/276 |
| 9,983,056 B2* | 5/2018 | Froehlich | ............ | G01J 3/0205 |
| 10,139,392 B2* | 11/2018 | Kaariainen | ............ | G01N 21/62 |
| 10,234,381 B2* | 3/2019 | Koulikov | .................. | G01J 3/42 |
| 2006/0181710 A1* | 8/2006 | Kachanov | .............. | G01N 21/39 |
| | | | | 356/437 |
| 2012/0261578 A1* | 10/2012 | Scott | ................. | G01N 21/3504 |
| | | | | 250/339.07 |
| 2012/0300209 A1* | 11/2012 | Witinski | ................ | G01N 21/39 |
| | | | | 356/409 |
| 2017/0059403 A1* | 3/2017 | Froehlich | ............ | H01S 5/06804 |
| 2018/0136113 A1* | 5/2018 | Bond | .................... | G01N 21/031 |
| 2019/0145935 A1* | 5/2019 | Csutak | ............... | G01N 29/2418 |
| | | | | 73/24.02 |
| 2019/0271672 A1* | 9/2019 | Wapelhorst | ............ | G01N 21/31 |

FOREIGN PATENT DOCUMENTS

| | | | | |
|---|---|---|---|---|
| WO | WO-2011092599 A1 * | 8/2011 | .......... | B01F 13/0827 |
| WO | WO-2016081632 A1 * | 5/2016 | .......... | H01S 5/0683 |

\* cited by examiner

LASER ABSORPTION SPECTROSCOPY ISOTOPIC GAS ANALYZER

CROSS-REFERENCES TO RELATED APPLICATIONS

This application is a continuation application of US Non-provisional application Ser. No. 16/407,144, filed May 8, 2019, which claims the benefit of, and priority to, U.S. non-provisional patent application Ser. No. 15/854,801, filed Dec. 27, 2017, which claims the benefit of, and priority to, U.S. provisional Patent application No. 62/535,505 filed Jul. 21, 2017, the contents of both of which are hereby incorporated by reference.

BACKGROUND OF THE INVENTION

The present invention relates generally to trace gas detection and more specifically to laser absorption spectroscopy systems and methods.

Optical absorption spectroscopy involves passing radiation through a sample, e.g., an analyte and measuring absorption property of the sample as a function of the radiation wavelength. For example, trace gas detection can be spectroscopically performed by taking measurements to detect the presence or absence of spectral absorption lines corresponding to the gas species of interest. Trace gas detection can be spectroscopically performed by taking measurements to quantify spectral absorption lines corresponding to the gas species of interest and to compute concentrations of analytes, gas pressure, and gas temperature. Spectroscopic analysis of isotopologues can also be performed. However, because the integral line intensities of absorption gas lines are sensitive to the gas temperature, and the line shapes of those lines are sensitive to the gas temperature, the gas pressure, and the gas composition, measurements of the isotopic ratio with high accuracy require highly accurate measurements of the analyzed gas temperature and pressure. In addition, such measurements of the integral intensities of different lines also require very precise measurements of laser frequency. Moreover, because the natural abundance for isotopes can be very different, the integral line intensities of absorption gas lines of different isotopologues can also be very different, because the integral intensities are the products of the line strengths, gas concentration and isotopologue abundance. That is why it might be hard to precisely measure the integral intensities of the absorption lines of less abundant isotopologues and as a result of that to precisely measure the ratio of concentrations of two isotopologues with quite different abundances.

Accordingly it is desirable to provide improved spectroscopy systems and methods for measuring concentrations of different isotopologues in their gas phase.

BRIEF SUMMARY OF THE INVENTION

The present invention provides systems and methods for measuring the isotope ratios of one or more trace gases.

Embodiments of the present invention provide systems and devices for detecting the isotopic ratios of the analyzed gas with high accuracy using an optical cavity, which contains a gas mixture to be analyzed, one or more lasers coupled to one or more cavities, and one or more light sensitive detectors. The optical cavity can be a resonant optical cavity. The resonant cavity can be any type of cavity with two or more cavity mirrors, including a linear or a ring cavity. A laser that is capable of being frequency-scanned can be coupled to the cavity though one of the cavity mirrors. A detection method can be based on any of a variety of cavity enhanced optical spectroscopy (CEOS) methods, for example, cavity ring-down spectroscopy (CRDS) methods, cavity phase shift spectroscopy methods, cavity enhanced absorption spectroscopy (CEAS) methods, integrated cavity output spectroscopy (ICOS), or cavity enhanced photo-acoustic spectroscopy (CE-PAS) methods. A detection method can also be based on tunable diode laser absorption spectroscopy (TDLAS) methods with or without using a multipass cell. Photo-acoustic spectroscopy (PAS) can also be used as a detection method.

The approach of one embodiment is based on the fact that spectral line intensities of different rotational-vibrational bands of an isotopologue can be quite different and different rotational-vibrational bands may occupy different spectral regions. FIGS. 1-5 show line intensities of different rotational-vibrational transitions for different rotational-vibrational bands for $^{12}C^{16}O_2$ isotopologue, where "T" is the absolute temperature of the gas. So, it may be preferable to measure strong rotational-vibrational bands of the less abundant isotopologue in one spectral region and weak rotational-vibrational bands of the more abundant isotopologue in another spectral region.

DETAILED DESCRIPTION OF THE INVENTION

Figure 1:
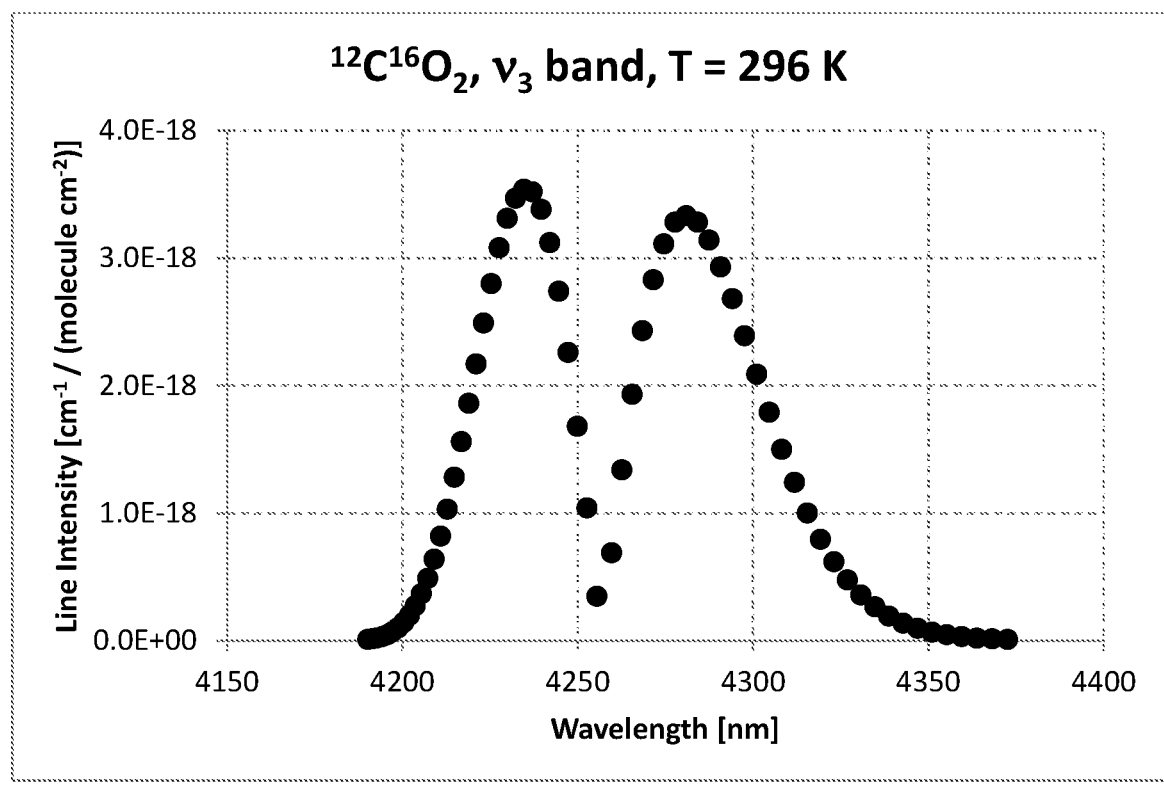
FIG. 1. Line intensities of different rotational-vibrational transitions from one rotational level in the ground vibrational state to one rotational level in the vibrationally excited state $v_3$ of $^{12}C^{16}O_2$ isotopologue at 296 K.
Figure 2:
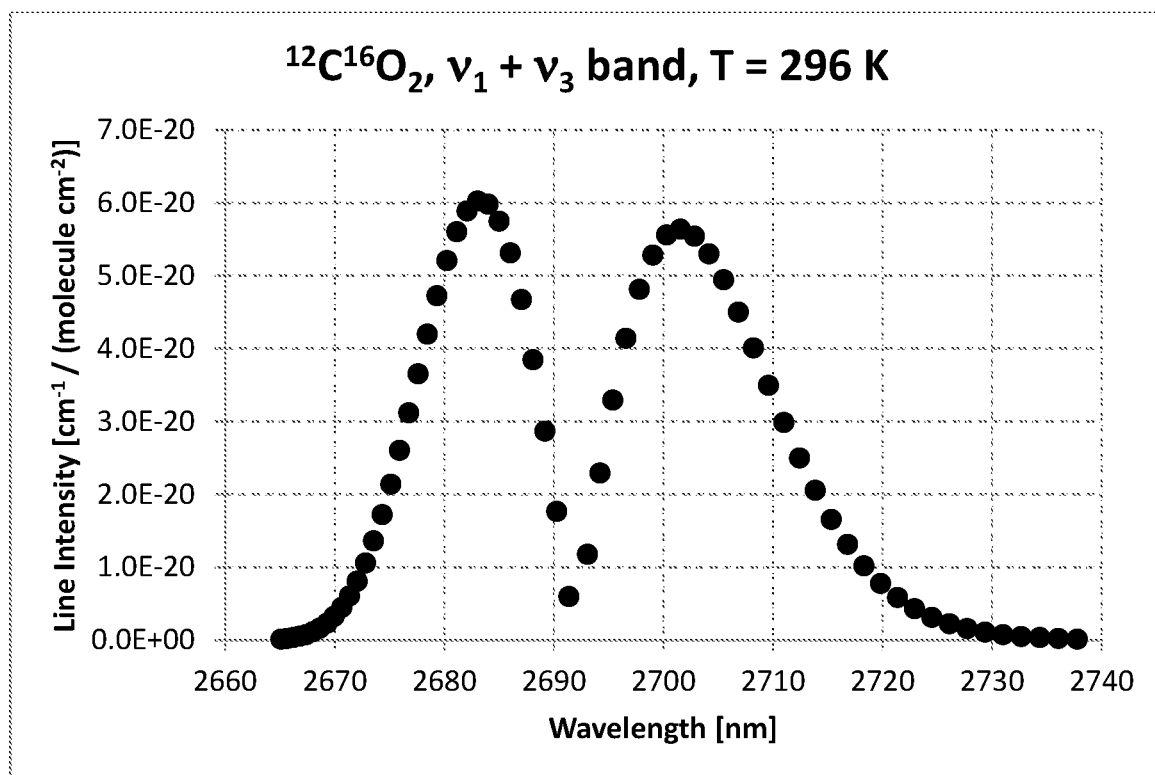
FIG. 2. Line intensities of different rotational-vibrational transitions from one rotational level in the ground vibrational state to one rotational level in the vibrationally excited state $v_1+v_3$ of $^{12}C^{16}O_2$ isotopologue at 296 K.
Figure 3:
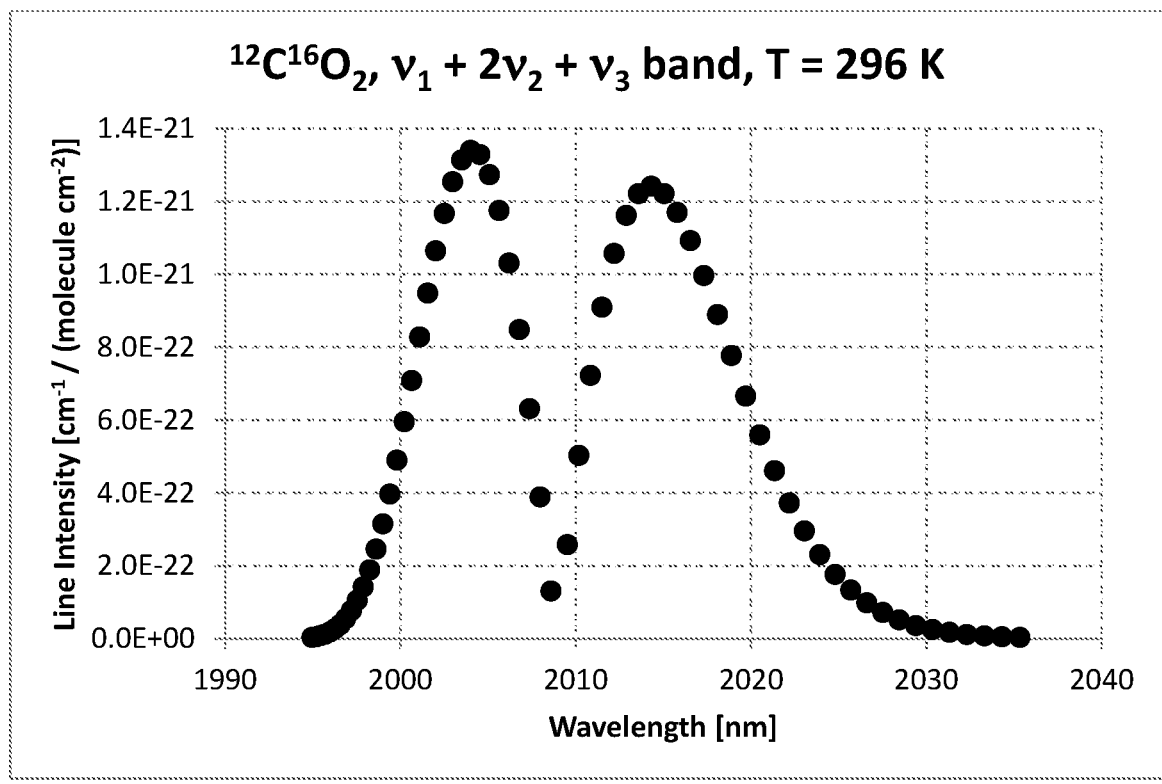
FIG. 3. Line intensities of different rotational-vibrational transitions from one rotational level in the ground vibrational state to one rotational level in the vibrationally excited state $v_1+2v_2+v_3$ of $^{12}C^{16}O_2$ isotopologue at 296 K.
Figure 4:
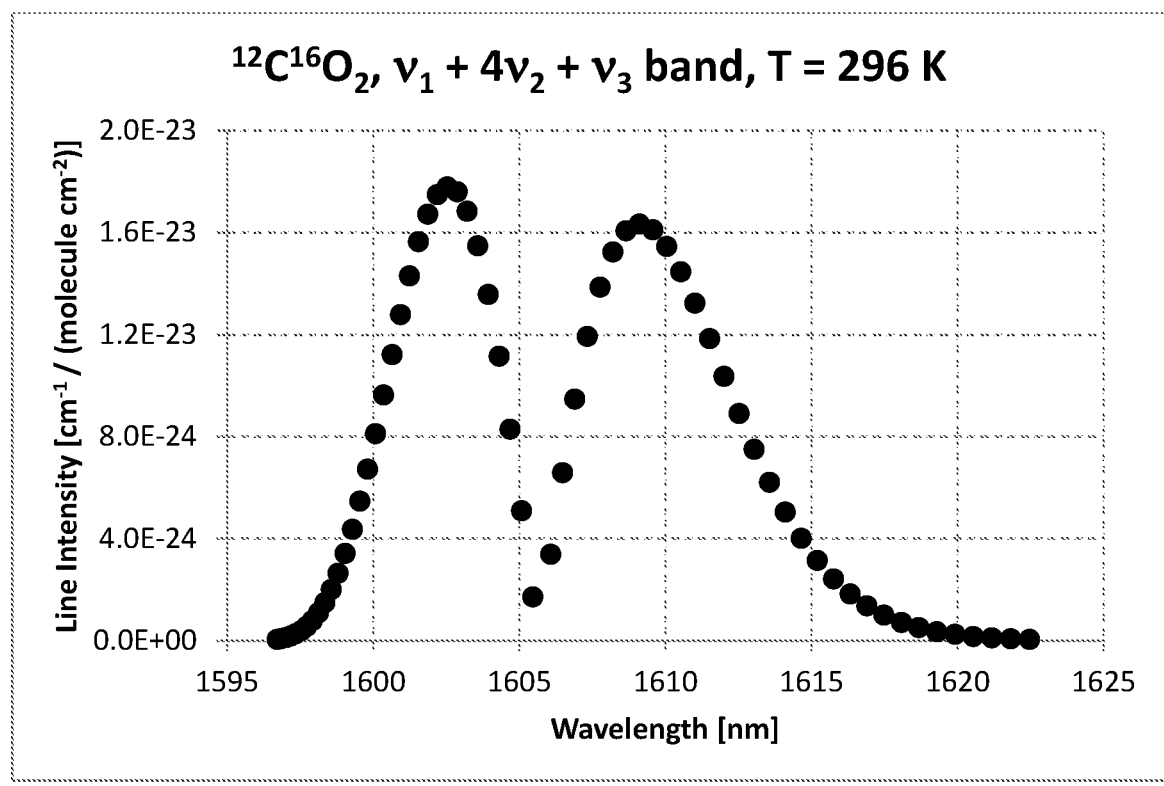
FIG. 4. Line intensities of different rotational-vibrational transitions from one rotational level in the ground vibrational state to one rotational level in the vibrationally excited state $v_1+4v_2+v_3$ of $^{12}C^{16}O_2$ isotopologue at 296 K.
Figure 5:
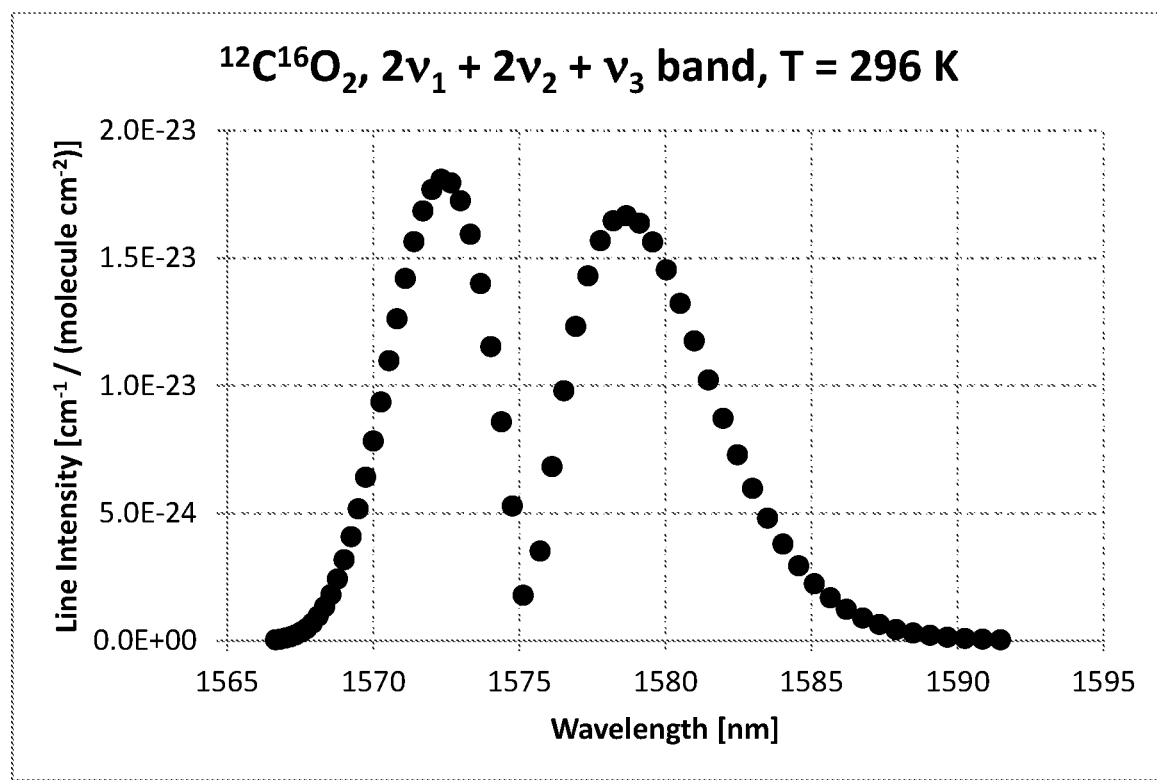
FIG. 5. Line intensities of different rotational-vibrational transitions from one rotational level in the ground vibrational state to one rotational level in the vibrationally excited state $2v_1+2v_2+v_3$ of $^{12}C^{16}O_2$ isotopologue at 296 K.
Figure 6:
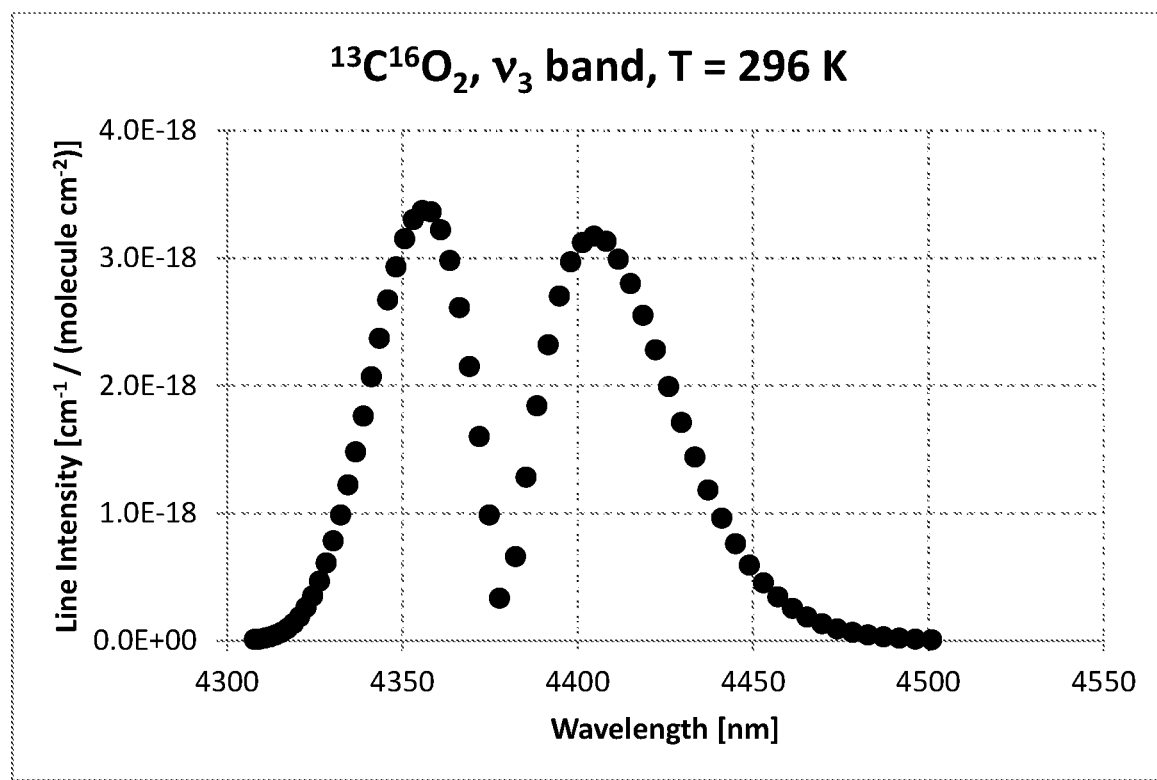
FIG. 6. Line intensities of different rotational-vibrational transitions from one rotational level in the ground vibrational state to one rotational level in the vibrationally excited state $v_3$ of $^{13}C^{16}O_2$ isotopologue at 296 K.
Figure 7:
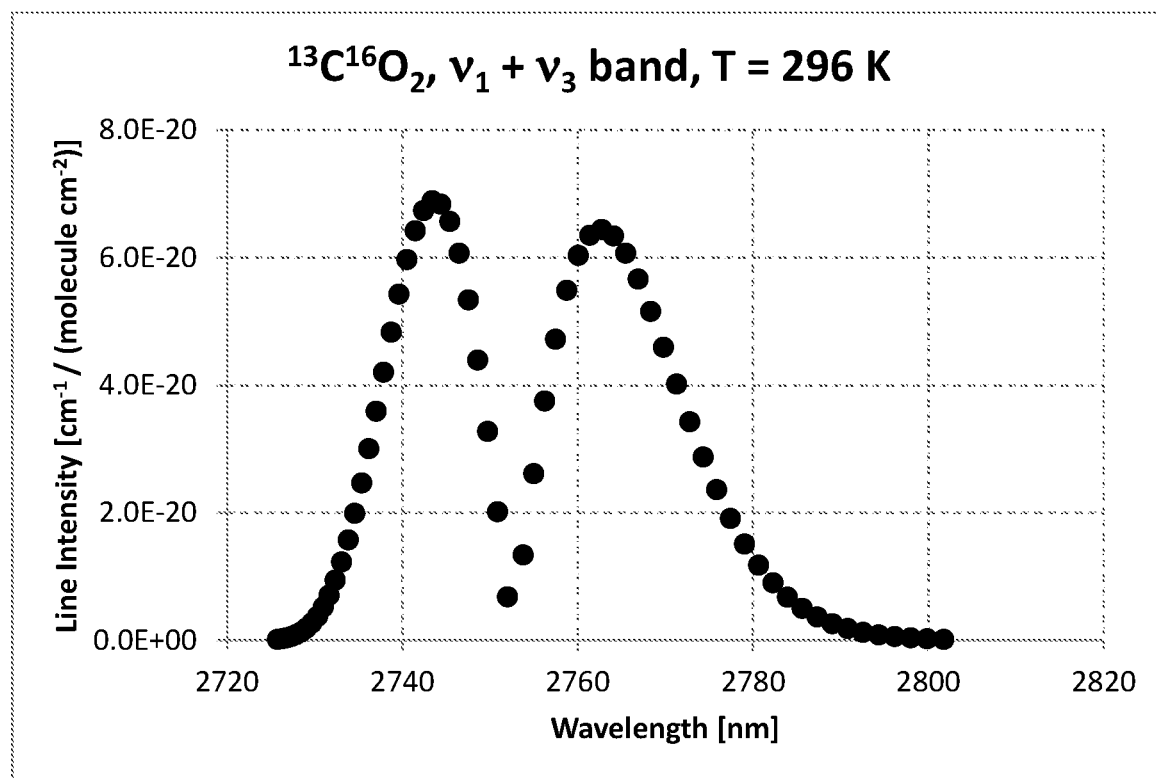
FIG. 7. Line intensities of different rotational-vibrational transitions from one rotational level in the ground vibrational state to one rotational level in the vibrationally excited state $v_1+v_3$ of $^{13}C^{16}O_2$ isotopologue at 296 K.
Figure 8:
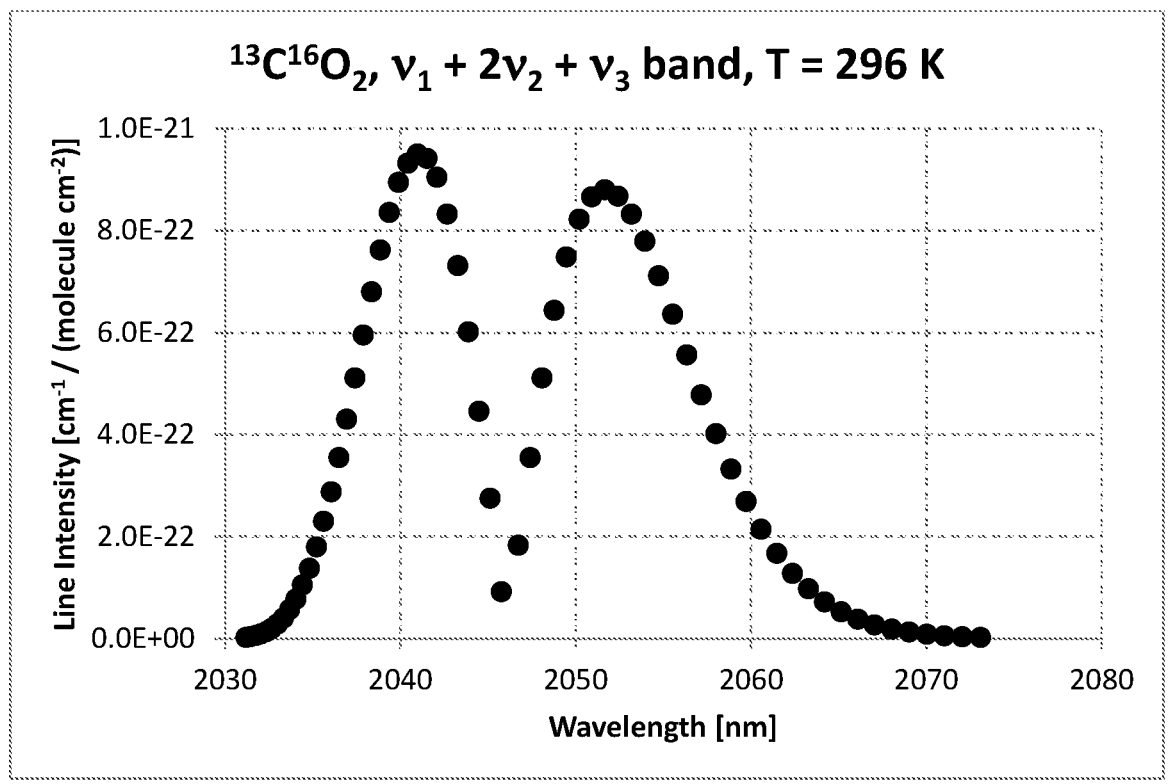
FIG. 8. Line intensities of different rotational-vibrational transitions from one rotational level in the ground vibrational state to one rotational level in the vibrationally excited state $v_1+2v_2+v_3$ of $^{13}C^{16}O_2$ isotopologue at 296 K.
Figure 9:
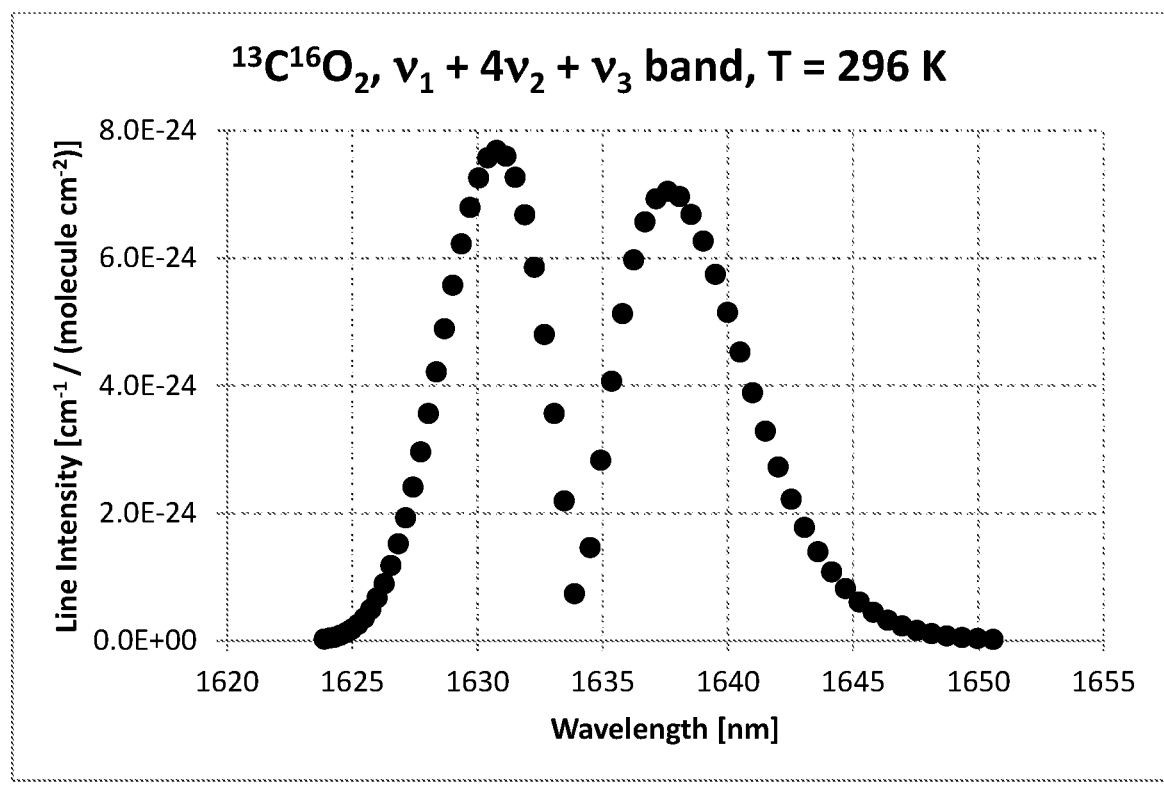
FIG. 9. Line intensities of different rotational-vibrational transitions from one rotational level in the ground vibrational state to one rotational level in the vibrationally excited state $v_1+4v_2+v_3$ of $^{13}C^{16}O_2$ isotopologue at 296 K.
Figure 10:
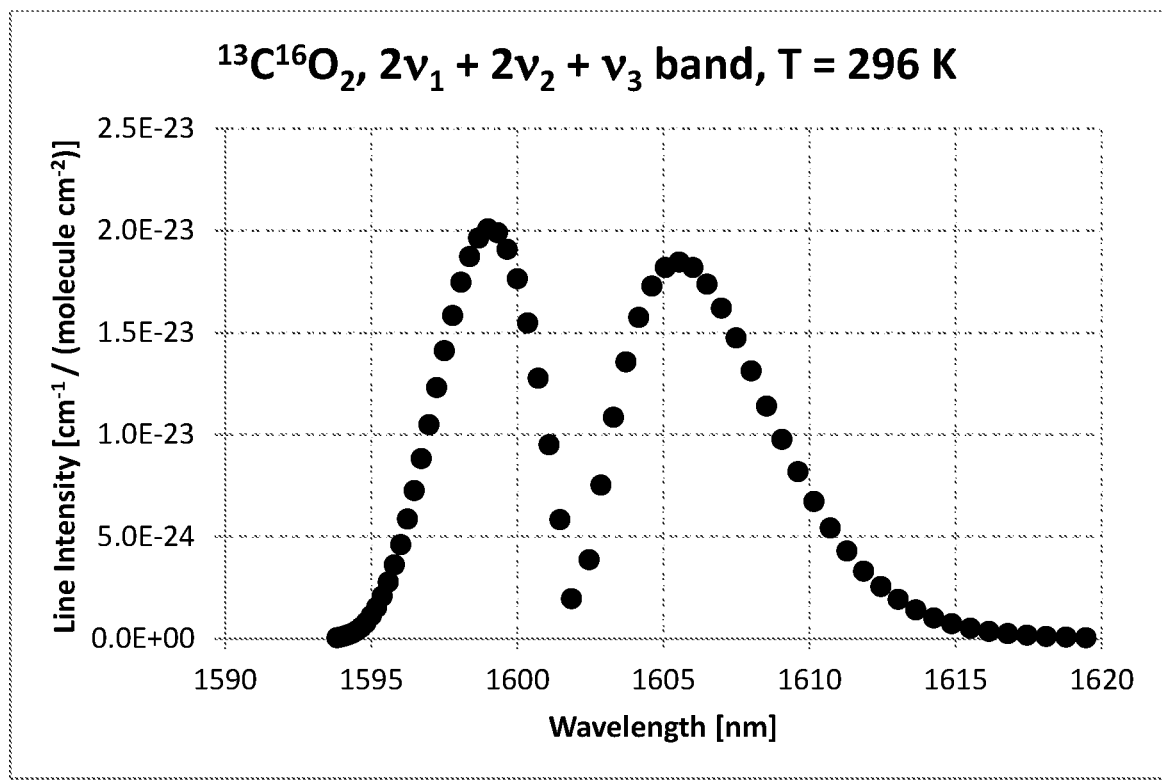
FIG. 10. Line intensities of different rotational-vibrational transitions from one rotational level in the ground vibrational state to one rotational level in the vibrationally excited state $2v_1+2v_2+v_3$ of $^{13}C^{16}O_2$ isotopologue at 296 K.

Here and further we use the term "the spectral line intensity" in units of $[cm^{-1}/(molecule\ cm^{-2})]$ similar to what was given in FIG. 1 in the Appendix to the article on the 1996 Edition of HITRAN in the Journal of Quantitative Spectroscopy and Radiative Transfer vol. 60, pp. 665-710 (1998). However, in our case the spectral line intensities are specified per an isotopologue molecule, while the spectral line intensities that appear in HITRAN are weighted according to the natural terrestrial isotopic abundances.

Systems and methods described herein may include or employ one or more spectrometers measuring rotational-vibrational spectra of different isotolologues in the gas phase. The rotational-vibrational spectra are often resolved into lines due to transitions from one rotational level in the ground vibrational state to one rotational level in the vibrationally excited state. The lines corresponding to a given vibrational transition form a band. The gas analyzer system measures rotational-vibrational spectra of isotopologues in the gas phase at least at two non-overlapping spectral regions: in a first spectral region the system measures at least one rotational-vibrational line of a less abundant isotopologue, and in a second spectral region the system measures at least one rotational-vibrational line of a more abundant isotopologue. Other lines of other isotopologues and other chemical species can also be measured in both spectral regions. To improve the system performance, these two lines belong to different vibrational modes chosen in such a way that the spectral line intensity of the strongest rotational-vibrational line of the vibrational mode of the less abundant isotopologue is at least two or more times stronger than the spectral line intensity of the strongest rotational-vibrational line of the vibrational mode of the more abundant isotopologue. This approach permits to improve both the precision and the accuracy of the isotope ratio measurements because the line intensities of two measured lines might be closer to each other, in comparison with the case when two lines of the same vibrational modes of two isotopologues are measured. Notice, in general, for spectral analysis one can choose rotational-vibrational lines with quite different spectral line intensities from the same vibrational modes of different isotopologues. However, in that case these lines usually have quite different pressure broadening and temperature dependences. So, the precise isotopic ratio analysis would require extremely accurate temperature and pressure stabilizations of the tested gas.

FIGS. 1-10 show examples of the line intensities of different vibrational modes of the two most abundant isotopologues of carbon dioxide in Mid-IR and NIR-IR spectral regions. Circles represent different rotational-vibrational transitions from one rotational level in the ground vibrational state to another rotational level in the vibrationally excited state. The line intensities were obtained from the HITRAN database. The energy change of rotation can be either subtracted from or added to the energy change of vibration, giving the P- and R-branches of the spectrum, respectively. Both P- and R branches are shown. Taking to account that abundance of carbon dioxide isopologues, according to HITAN is 98.42% and 1.106% for $^{12}C^{16}O_2$ and $^{13}C^{16}O_2$, respectively, the following pairs of rotational-vibrational bands can be considered for spectral analysis according to one of the embodiments:
1) $v_1+v_3$ vibrational mode of $^{12}C^{16}O_2$ and $v_3$ vibrational mode of $^{13}C^{16}O_2$;
2) $v_1+2v_2+v_3$ vibrational mode of $^{12}C^{16}O_2$ and $v_3$ vibrational mode of $^{13}C^{16}O_2$;
3) $v_1+4v_2+v_3$ vibrational mode of $^{12}C^{16}O_2$ and $v_3$ vibrational mode of $^{13}C^{16}O_2$;
4) $2v_1+2v_2+v_3$ vibrational mode of $^{12}C^{16}O_2$ and $v_3$ vibrational mode of $^{13}C^{16}O_2$;
5) $v_1+2v_2+v_3$ vibrational mode of $^{12}C^{16}O_2$ and $v_1+v_3$ vibrational mode of $^{13}C^{16}O_2$;
6) $v_1+4v_2+v_3$ vibrational mode of $^{12}C^{16}O_2$ and $v_1+v_3$ vibrational mode of $^{13}C^{16}O_2$;
7) $2v_1+2v_2+v_3$ mode of for $^{12}C^{16}O_2$ and $v_1+v_3$ mode of $^{13}C^{16}O_2$;
8) $v_1+4v_2+v_3$ vibrational mode of $^{12}C^{16}O_2$ and $v_1+2v_2+v_3$ vibrational mode of $^{13}C^{16}O_2$;
9) $2v_1+2v_2+v_3$ vibrational mode of $^{12}C^{16}O_2$ and $v_1+2v_2+v_3$ vibrational mode of $^{13}C^{16}O_2$;

where $v_1$, $v_2$, and $v_3$ represent normal modes of the $CO_2$ molecule: symmetric stretch, bend, and asymmetric stretch, respectively.

By comparing FIGS. 1-10 one can easily see that the bands in these pairs are spectrally well separated and the line intensity of the strongest line in the band of the less abundant isotopologue is at least as twice as strong as the line intensity of the strongest line in the band of the more abandon isotopologue.

Line intensity is the integrated absorption cross section across a line. Because the line intensities are temperature dependent, the line intensities of different lines should be compared at the temperature of the measured gas. The temperature dependence coefficient is defined as a derivative of the line intensity over temperature divided by the line intensity itself. The temperature dependence coefficients depend on temperature and according to one embodiment they are compared at the temperature of a measured gas mixture.

After a pair of rotational-vibrational bands corresponding to two different isotopologues was selected for spectral analysis, spectral ranges for measuring the isotopologue concentration ratios can be chosen according to another embodiment: at least one of the rotational-vibrational lines of the band of the less abundant isotopologue is located and measured in the first spectral region, and at least one of the rotational-vibrational lines of the band of the more abundant isotopologue is located and measured in the second spectral region.

According to another embodiment the ratio of an absorption spectrum of the less abundant isotopologue in the first selected spectral region to the sum of the absorption spectra of all other isotopologues of the same chemical substance exceeds two somewhere in the first selected spectral region, and the ratio of an absorption spectrum of the more abundant isotopologue in the second selected spectral region to the sum of the absorption spectra of all other isotopologues of the same chemical substance exceeds two somewhere in the second selected spectral region. These spectra are compared at the temperature and at the pressure of the measured gas or gas mixture.

Figure 11:
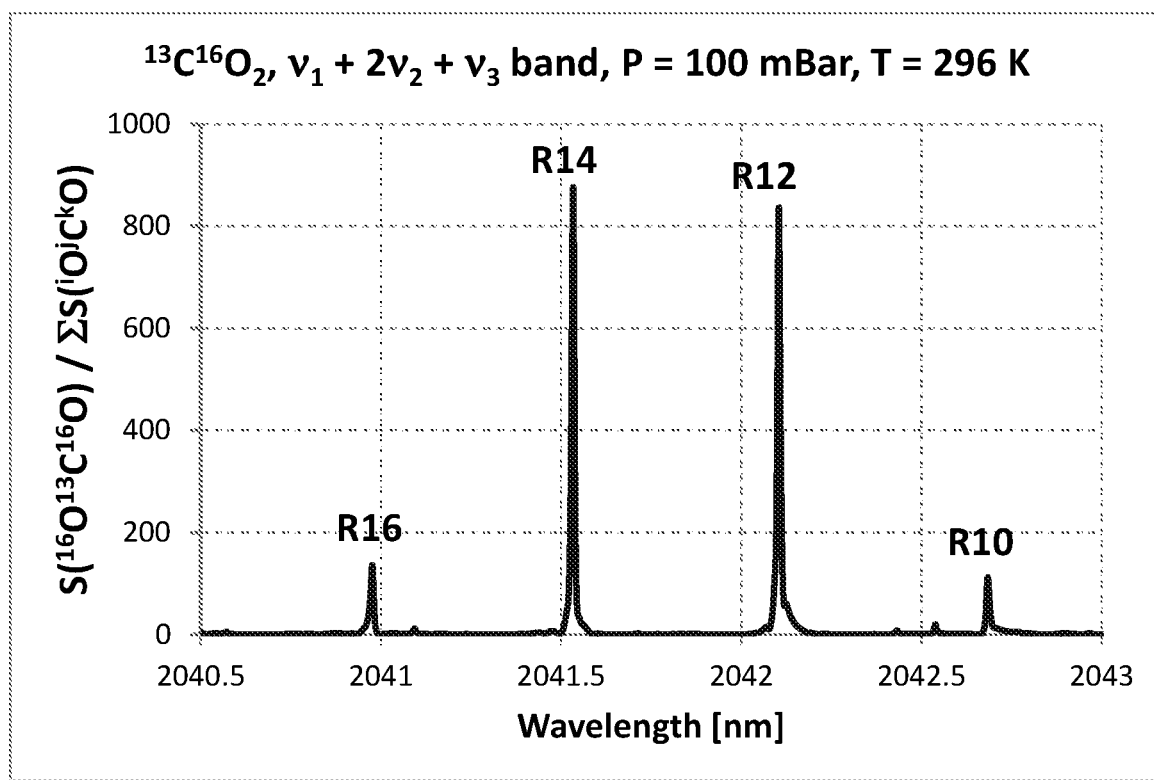
FIG. 11. The ratio of the spectrum of the $^{13}C^{16}O_2$ isotopologue to the sum of spectra of all other isopologues of $CO_2$ from 2040.5 nm to 2043 nm at a pressure of 100 m Bar and a temperature of 296 K. $R_x$ symbols show positions where the corresponding rotational-vibrational transitions, from one rotational level in the ground vibrational state to another rotational level in the vibrationally excited state $v_1+2v_2+v_3$ of $^{13}C^{16}O_2$ isotopologue, are located.
Figure 14:
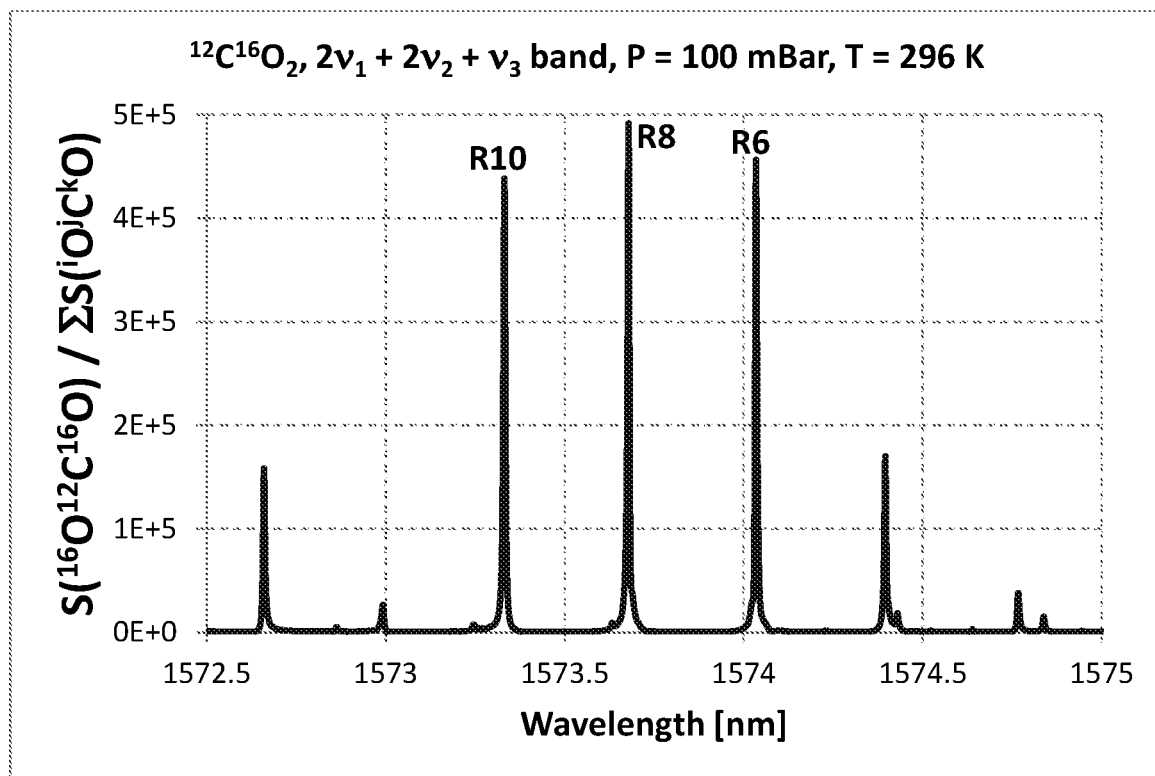
FIG. 14. The ratio of the spectrum of the $^{12}C^{16}O_2$ isotopologue to the sum of spectra of all other isopologues of $CO_2$ from 1572.5 nm to 1575 nm at a pressure of 100 mBar and a temperature of 296 K. $R_x$ symbols show positions where the corresponding rotational-vibrational transitions, from one rotational level in the ground vibrational state to another rotational level in the vibrationally excited state $2v_1+2v_2+v_3$ of $^{13}C^{16}O_2$ isotopologue, are located.

As an example, the rotational-vibrational band corresponding to the $2v_1+2v_2+v_3$ vibrational mode of $^{12}C^{16}O_2$ and the rotational-vibrational band corresponding to the $v_1+2v_2+v_3$ vibrational mode of $^{13}C^{16}O_2$ are selected to illustrate the method. FIG. 11 shows the ratio of an absorption spectrum of the less abundant isotopologue, $^{13}C^{16}O_2$ in the first selected spectral region to the sum of the absorption spectra of all other isotopologues of carbon dioxide at a pressure of 100 mBar and at a temperature of 296 K. FIG. 14 shows the ratio of an absorptions spectrum of the more abundant isotopologue, $^{12}C^{16}O_2$, in the second selected spectral region to the sum of spectra of all other isotopologues of carbon dioxide at a pressure of 100 mBar and at a temperature of 296 K. P stands for gas pressure. All figures from 11 to 18 were created for gas pressure P=100 mBar, and gas temperature T=296K. S( ) is an absorption spectrum of a particular isotopologue. Σ stands for sum, while indexes i, j, and k describe different isotopes of hydrogen, oxygen, or carbon atoms. One can see that at some spectral points corresponding to some rotational-vibrational lines the ratios exceed number two. The sums of spectra were calculated taking into account the abundances of different isotopologues.

As another example, the R12 rotational-vibrational line of the $v_1+2v_2+v_3$ vibrational mode of $^{13}C^{16}O_2$ and the R10 rotational-vibrational line of the $2v_1+2v_2+v_3$ vibrational mode of $^{12}C^{16}O_2$ can be selected for isotopic ratio analysis. The first spectral range to measure lines of $^{13}C^{16}O_2$ is from 2040.5 nm to 2043 nm. The second spectral range to measure lines of $^{12}C^{16}O_2$ is from 1572.5 nm to 1575 nm. Notice, these rotational-vibrational lines correspond to quite different transitions from one rotational level in the ground vibrational state to one rotational level in the vibrationally excited state. For example, the R12 rotational-vibrational line of the $v_1+2v_2+v_3$ vibrational mode of $^{13}C^{16}O_2$ corresponds to the transition $(v_1=0, v_2=0, v_3=0, J=12) \rightarrow (v_1=1, v_2=2, v_3=1, J=13)$ from the rotation level J=12 of the ground state to the rotation level J=13 of the vibrationally excited $v_1+2v_2+v_3$ vibrational mode, or to $(\Delta v_1=+1, \Delta v_2=+2, \Delta v_1=+1, \Delta J=+1)$ transition, while the R10 rotational-vibrational line of $2v_1+2v_2+v_3$ vibrational mode of $^{12}C^{16}O_2$ corresponds to the transition $(v_1=0, v_2=0, v_3=0, J=10) \rightarrow (v_1=2, v_2=2, v_3=1, J=11)$ from the rotation level J=10 of the ground state to the rotation level J=11 of the vibrationally excited $2v_1+2v_2+v_3$ vibrational mode, or to $(\Delta v_1=+2, \Delta v_2=+2, \Delta v_1=+1, \Delta J=+1)$ transition.

According to a general convention rotational-vibrational bands can be divided on three branches: R-branch, P-branch, and Q-branch:

R branch: when $\Delta J=+1$, i.e. the rotational quantum number in the ground state is one more than the rotational quantum number in the excited state;

P branch: when $\Delta J=-1$, i.e. the rotational quantum number in the ground state is one less than the rotational quantum number in the excited state;

Q branch: when $\Delta J=0$, i.e. the rotational quantum number in the ground state is the same as the rotational quantum number in the excited state.

The following tables show some parameters of the selected vibration modes of two isotpologues.

TABLE 1

$v_1 + 2v_2 + v_3$ band of $^{13}C^{16}O_2$: branch symbol (P or R), J is the quantum number associated with the total angular momentum, wavelength λ[nm], line strength S[cm$^{-1}$/ (molecule cm$^{-2}$)], air-broadened half-width $\gamma_{air}$[cm$^{-1}$ atm$^{-1}$], self-broadened half-width $\gamma_{self}$[cm$^{-1}$ atm$^{-1}$], and temperature dependence coefficient dS/SdT [K$^{-1}$].

|   | J  | λ         | S        | $\gamma_{air}$ | $\gamma_{self}$ | dS/SdT    |
|---|----|-----------|----------|--------|---------|-----------|
| P | 38 | 2060.5951 | 2.14E−22 | 0.0681 | 0.083   | 5.17E−03  |
| P | 36 | 2059.7220 | 2.69E−22 | 0.0683 | 0.085   | 4.12E−03  |
| P | 34 | 2058.8614 | 3.32E−22 | 0.0685 | 0.087   | 3.34E−03  |
| P | 32 | 2058.0131 | 4.02E−22 | 0.0687 | 0.089   | 2.30E−03  |
| P | 30 | 2057.1772 | 4.78E−22 | 0.0690 | 0.091   | 1.55E−03  |
| P | 28 | 2056.3536 | 5.56E−22 | 0.0693 | 0.093   | 8.33E−04  |
| P | 26 | 2055.5421 | 6.36E−22 | 0.0699 | 0.094   | 1.46E−04  |
| P | 24 | 2054.7428 | 7.11E−22 | 0.0706 | 0.096   | −5.22E−04 |
| P | 22 | 2053.9556 | 7.79E−22 | 0.0715 | 0.098   | −1.19E−03 |
| P | 20 | 2053.1805 | 8.32E−22 | 0.0727 | 0.099   | −1.68E−03 |
| P | 18 | 2052.4173 | 8.67E−22 | 0.0741 | 0.101   | −2.15E−03 |
| P | 16 | 2051.6662 | 8.80E−22 | 0.0758 | 0.103   | −2.64E−03 |
| P | 14 | 2050.9269 | 8.66E−22 | 0.0778 | 0.105   | −3.01E−03 |
| P | 12 | 2050.1996 | 8.22E−22 | 0.0798 | 0.107   | −3.40E−03 |
| P | 10 | 2049.4841 | 7.48E−22 | 0.0820 | 0.109   | −3.62E−03 |
| P | 8  | 2048.7805 | 6.43E−22 | 0.0842 | 0.112   | −3.91E−03 |
| P | 6  | 2048.0886 | 5.11E−22 | 0.0861 | 0.115   | −4.02E−03 |
| P | 4  | 2047.4086 | 3.55E−22 | 0.0877 | 0.117   | −4.20E−03 |
| P | 2  | 2046.7403 | 1.83E−22 | 0.0891 | 0.120   | −4.09E−03 |
| R | 0  | 2045.7599 | 9.22E−23 | 0.0925 | 0.125   | −4.34E−03 |
| R | 2  | 2045.1210 | 2.75E−22 | 0.0883 | 0.118   | −4.42E−03 |
| R | 4  | 2044.4938 | 4.46E−22 | 0.0870 | 0.116   | −4.18E−03 |
| R | 6  | 2043.8783 | 6.01E−22 | 0.0852 | 0.113   | −4.04E−03 |
| R | 8  | 2043.2746 | 7.31E−22 | 0.0831 | 0.110   | −3.96E−03 |
| R | 10 | 2042.6826 | 8.32E−22 | 0.0808 | 0.108   | −3.70E−03 |
| R | 12 | 2042.1023 | 9.04E−22 | 0.0788 | 0.106   | −3.40E−03 |
| R | 14 | 2041.5338 | 9.41E−22 | 0.0768 | 0.104   | −2.96E−03 |
| R | 16 | 2040.9770 | 9.50E−22 | 0.0749 | 0.102   | −2.93E−03 |
| R | 18 | 2040.4319 | 9.32E−22 | 0.0733 | 0.100   | −1.99E−03 |
| R | 20 | 2039.8987 | 8.94E−22 | 0.0721 | 0.099   | −1.66E−03 |
| R | 22 | 2039.3773 | 8.35E−22 | 0.0710 | 0.097   | −1.11E−03 |
| R | 24 | 2038.8677 | 7.62E−22 | 0.0702 | 0.095   | −4.88E−04 |
| R | 26 | 2038.3699 | 6.80E−22 | 0.0696 | 0.094   | 1.36E−04  |
| R | 28 | 2037.8841 | 5.95E−22 | 0.0691 | 0.092   | 7.79E−04  |
| R | 30 | 2037.4101 | 5.11E−22 | 0.0688 | 0.090   | 1.63E−03  |
| R | 32 | 2036.9481 | 4.30E−22 | 0.0686 | 0.088   | 2.37E−03  |
| R | 34 | 2036.4981 | 3.55E−22 | 0.0684 | 0.086   | 3.12E−03  |
| R | 36 | 2036.0600 | 2.88E−22 | 0.0682 | 0.084   | 4.17E−03  |
| R | 38 | 2035.6341 | 2.30E−22 | 0.0680 | 0.082   | 5.23E−03  |

TABLE 2

$2v_1 + 2v_2 + v_3$ band of $^{12}C^{16}O_2$: branch symbol (P or R), J is the quantum number associated with the total angular momentum, wavelength λ[nm], line strength S[cm$^{-1}$/ (molecule cm$^{-2}$)], air-broadened half-width $\gamma_{air}$[cm$^{-1}$ atm$^{-1}$], self-broadened half-width $\gamma_{self}$[cm$^{-1}$ atm$^{-1}$], and temperature dependence coefficient dS/SdT [K$^{-1}$].

|   | J  | λ         | S        | $\gamma_{air}$ | $\gamma_{self}$ | dS/SdT    |
|---|----|-----------|----------|--------|---------|-----------|
| P | 38 | 1584.0323 | 3.79E−24 | 0.0682 | 0.082   | 5.20E−03  |
| P | 36 | 1583.5076 | 4.80E−24 | 0.0686 | 0.084   | 4.10E−03  |
| P | 34 | 1582.9901 | 5.97E−24 | 0.0689 | 0.086   | 3.30E−03  |
| P | 32 | 1582.4799 | 7.28E−24 | 0.0695 | 0.088   | 2.42E−03  |
| P | 30 | 1581.9770 | 8.71E−24 | 0.0698 | 0.090   | 1.67E−03  |
| P | 28 | 1581.4815 | 1.02E−23 | 0.0703 | 0.092   | 9.13E−04  |
| P | 26 | 1580.9933 | 1.18E−23 | 0.0709 | 0.094   | 0.00E+00  |
| P | 24 | 1580.5127 | 1.32E−23 | 0.0716 | 0.096   | −7.84E−04 |
| P | 22 | 1580.0395 | 1.45E−23 | 0.0727 | 0.098   | −1.43E−03 |
| P | 20 | 1579.5739 | 1.56E−23 | 0.0741 | 0.100   | −1.33E−03 |
| P | 18 | 1579.1158 | 1.64E−23 | 0.0749 | 0.101   | −1.90E−03 |
| P | 16 | 1578.6654 | 1.67E−23 | 0.0766 | 0.104   | −2.49E−03 |
| P | 14 | 1578.2224 | 1.65E−23 | 0.0781 | 0.105   | −3.15E−03 |
| P | 12 | 1577.7872 | 1.57E−23 | 0.0797 | 0.108   | −3.31E−03 |
| P | 10 | 1577.3596 | 1.43E−23 | 0.0813 | 0.109   | −3.63E−03 |

TABLE 2-continued $2v_1 + 2v_2 + v_3$ band of $^{12}C^{16}O_2$: branch symbol (P or R), J is the quantum number associated with the total angular momentum, wavelength λ[nm], line strength S[cm$^{-1}$/(molecule cm$^{-2}$)], air-broadened half-width $\gamma_{air}$[cm$^{-1}$ atm$^{-1}$], self-broadened half-width $\gamma_{self}$[cm$^{-1}$ atm$^{-1}$], and temperature dependence coefficient dS/SdT [K$^{-1}$].

|   | J | λ | S | $\gamma_{air}$ | $\gamma_{self}$ | dS/SdT |
|---|---|---|---|---|---|---|
| P | 8 | 1576.9396 | 1.23E−23 | 0.0830 | 0.112 | −4.21E−03 |
| P | 6 | 1576.5273 | 9.80E−24 | 0.0854 | 0.115 | −4.02E−03 |
| P | 4 | 1576.1226 | 6.82E−24 | 0.0873 | 0.118 | −4.10E−03 |
| P | 2 | 1575.7256 | 3.51E−24 | 0.0920 | 0.123 | −4.14E−03 |
| R | 0 | 1575.1445 | 1.78E−24 | 0.0953 | 0.129 | −4.08E−03 |
| R | 2 | 1574.7667 | 5.28E−24 | 0.0884 | 0.120 | −4.32E−03 |
| R | 4 | 1574.3965 | 8.58E−24 | 0.0858 | 0.116 | −4.11E−03 |
| R | 6 | 1574.0340 | 1.15E−23 | 0.0838 | 0.114 | −3.60E−03 |
| R | 8 | 1573.6790 | 1.40E−23 | 0.0816 | 0.111 | −3.70E−03 |
| R | 10 | 1573.3317 | 1.59E−23 | 0.0800 | 0.108 | −3.91E−03 |
| R | 12 | 1572.9920 | 1.72E−23 | 0.0781 | 0.106 | −3.01E−03 |
| R | 14 | 1572.6598 | 1.80E−23 | 0.0766 | 0.104 | −2.89E−03 |
| R | 16 | 1572.3352 | 1.81E−23 | 0.0747 | 0.102 | −2.29E−03 |
| R | 18 | 1572.0180 | 1.77E−23 | 0.0738 | 0.100 | −2.35E−03 |
| R | 20 | 1571.7083 | 1.68E−23 | 0.0727 | 0.098 | −1.85E−03 |
| R | 22 | 1571.4060 | 1.56E−23 | 0.0718 | 0.097 | −1.33E−03 |
| R | 24 | 1571.1112 | 1.42E−23 | 0.0710 | 0.095 | −7.30E−04 |
| R | 26 | 1570.8236 | 1.26E−23 | 0.0703 | 0.093 | 0.00E+00 |
| R | 28 | 1570.5434 | 1.10E−23 | 0.0700 | 0.091 | 9.44E−04 |
| R | 30 | 1570.2704 | 9.35E−24 | 0.0694 | 0.089 | 1.66E−03 |
| R | 32 | 1570.0046 | 7.82E−24 | 0.0689 | 0.087 | 2.39E−03 |
| R | 34 | 1569.7459 | 6.41E−24 | 0.0685 | 0.085 | 3.23E−03 |
| R | 36 | 1569.4943 | 5.16E−24 | 0.0689 | 0.084 | 4.21E−03 |
| R | 38 | 1569.2497 | 4.08E−24 | 0.0679 | 0.081 | 5.08E−03 |

Table 1 and Table 2 show that both selected lines (R12 rotational-vibrational line of $v_1+2v_2+v_3$ vibrational mode of $^{13}C^{16}O_2$ and R10 rotational-vibrational line of $2v_1+2v_2+v_3$ vibrational mode) satisfy to another embodiment: the pressure broadening coefficients of these lines are different by no more than 50%.

Table 1 and Table 2 also show that both selected lines (R12 rotational-vibrational line of $v_1+2v_2+v_3$ vibrational mode of $^{13}C^{16}O_2$ and R10 rotational-vibrational line of $2v_1+2v_2+v_3$ vibrational mode) satisfy yet to another embodiment: the temperature dependence coefficients of these lines are different by no more than 50%.

Figure 12:
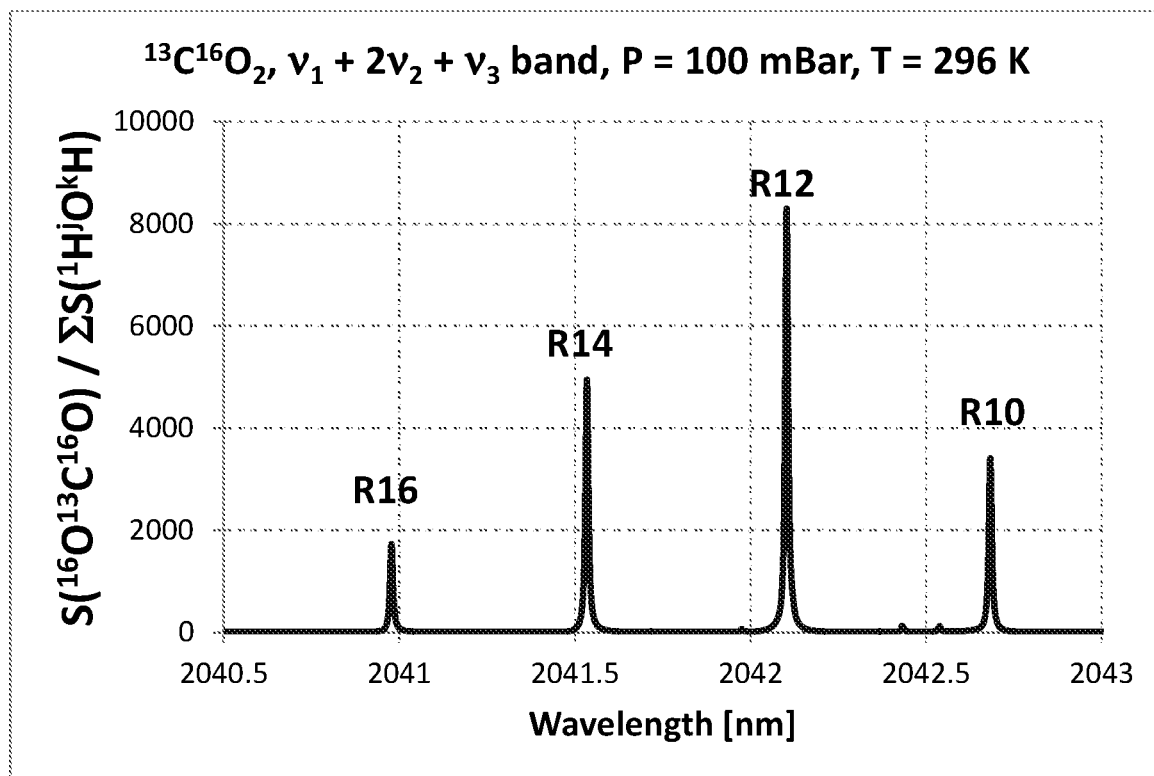
FIG. 12. The ratio of the spectrum of the $^{13}C^{16}O_2$ isotopologue to the sum of spectra of all isopologues of water from 2040.5 nm to 2043 nm at a pressure of 100 mBar and a temperature of 296 K. $R_N$ symbols show positions where the corresponding rotational-vibrational transitions, from one rotational level in the ground vibrational state to another rotational level in the vibrationally excited state $v_1+2v_2+v_3$ of $^{13}C^{16}O_2$ isotopologue, are located.
Figure 13:
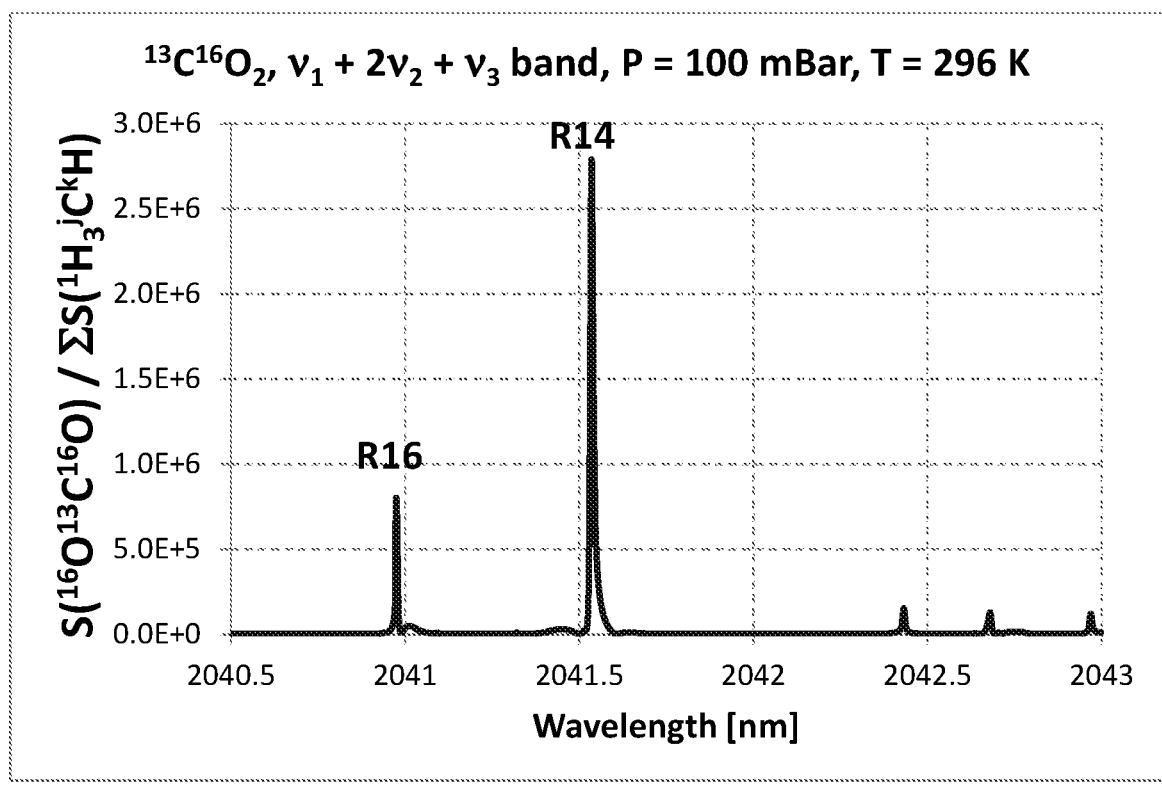
FIG. 13. The ratio of the spectrum of the $^{13}C^{16}O_2$ isotopologue to the sum of spectra of all isopologues of methane from 2040.5 nm to 2043 nm at a pressure of 100 mBar and a temperature of 296 K. $R_N$ symbols show positions where the corresponding rotational-vibrational transitions, from one rotational level in the ground vibrational state to another rotational level in the vibrationally excited state $v_1+2v_2+v_3$ of $^{13}C^{16}O_2$ isotopologue, are located.
Figure 15:
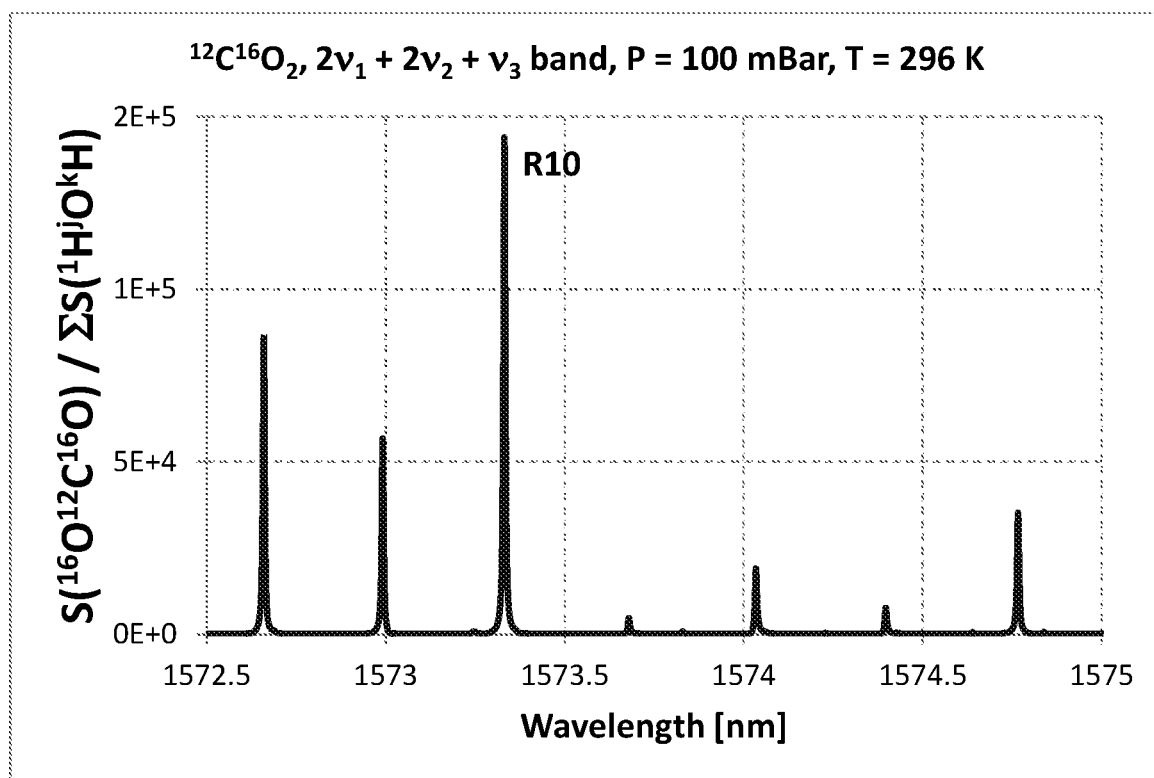
FIG. 15. The ratio of the spectrum of the $^{12}C^{16}O_2$ isotopologue to the sum of spectra of all isopologues of water from 1572.5 nm to 1575 nm at a pressure of 100 mBar and a temperature of 296 K. $R_x$ symbols show positions where the corresponding rotational-vibrational transitions, from one rotational level in the ground vibrational state to another rotational level in the vibrationally excited state $2v_1+2v_2+v_3$ of $^{13}C^{16}O_2$ isotopologue, are located.
Figure 16:
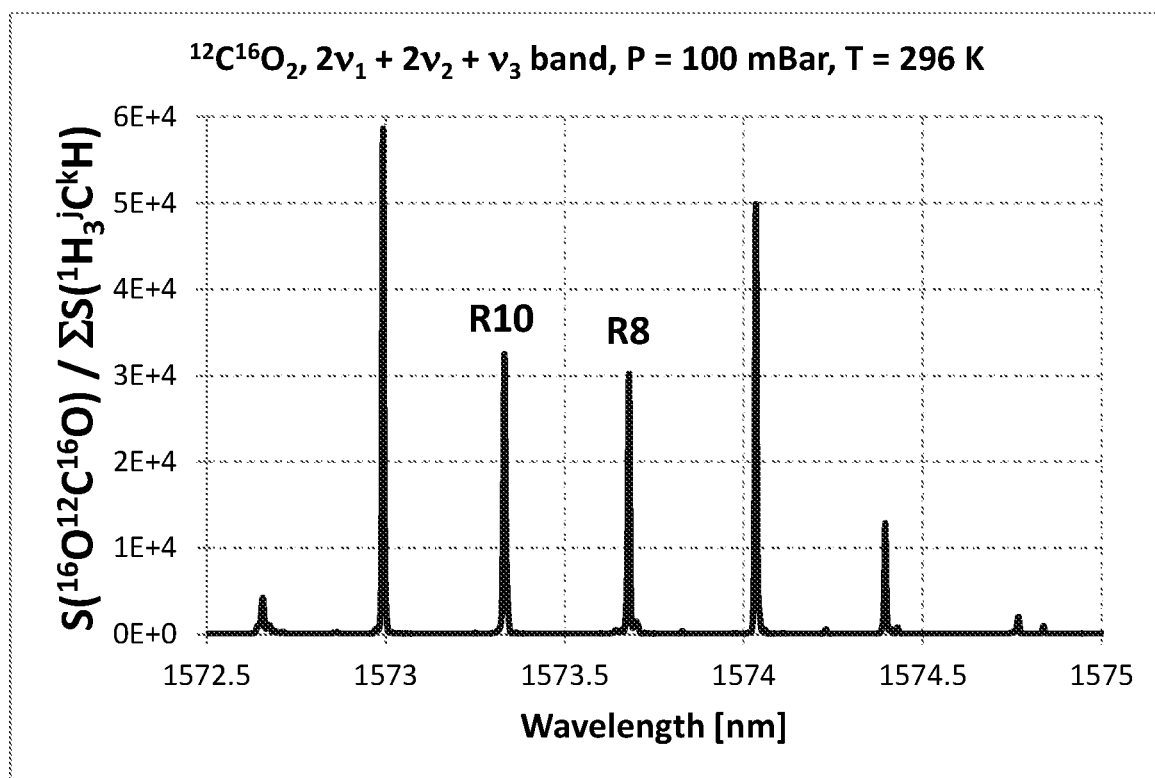
FIG. 16. The ratio of the spectrum of the $^{12}C^{16}O_2$ isotopologue to the sum of spectra of all isopologues of methane from 1572.5 nm to 1575 nm at a pressure of 100 mBar and a temperature of 296 K. $R_x$ symbols show positions where the corresponding rotational-vibrational transitions, from one rotational level in the ground vibrational state to another rotational level in the vibrationally excited state $2v_1+2v_2+v_3$ of $^{13}C^{16}O_2$ isotopologue, are located.

If other inference species are present in the gas or in the mixture, similar spectral analysis may help better choose spectral regions. FIG. 12 and FIG. 13 show the ratios of the absorption spectrum of $^{13}C^{16}O_2$ in the first selected spectral region to the sum of absorption spectra of all water isotopologues and to the sum of absorption spectra of all methane isotopologues at a pressure of 100 mBar and at a temperature of 296 K. FIG. 15 and FIG. 16 show the ratios of the absorption spectrum of $^{12}C^{16}O_2$ in the second selected spectral region to the sum of absorption spectra of all $H_2O$ isotopologues and to the sum of absorption spectra of all $CH_4$ isotopologues at a pressure of 100 mBar and at a temperature of 296 K. Concentrations of $CO_2$, $H_2O$, and $CH_4$ in FIGS. 12-16 are the same. The sums were calculated taking into account abundances of different isotopologues.

Figure 17:
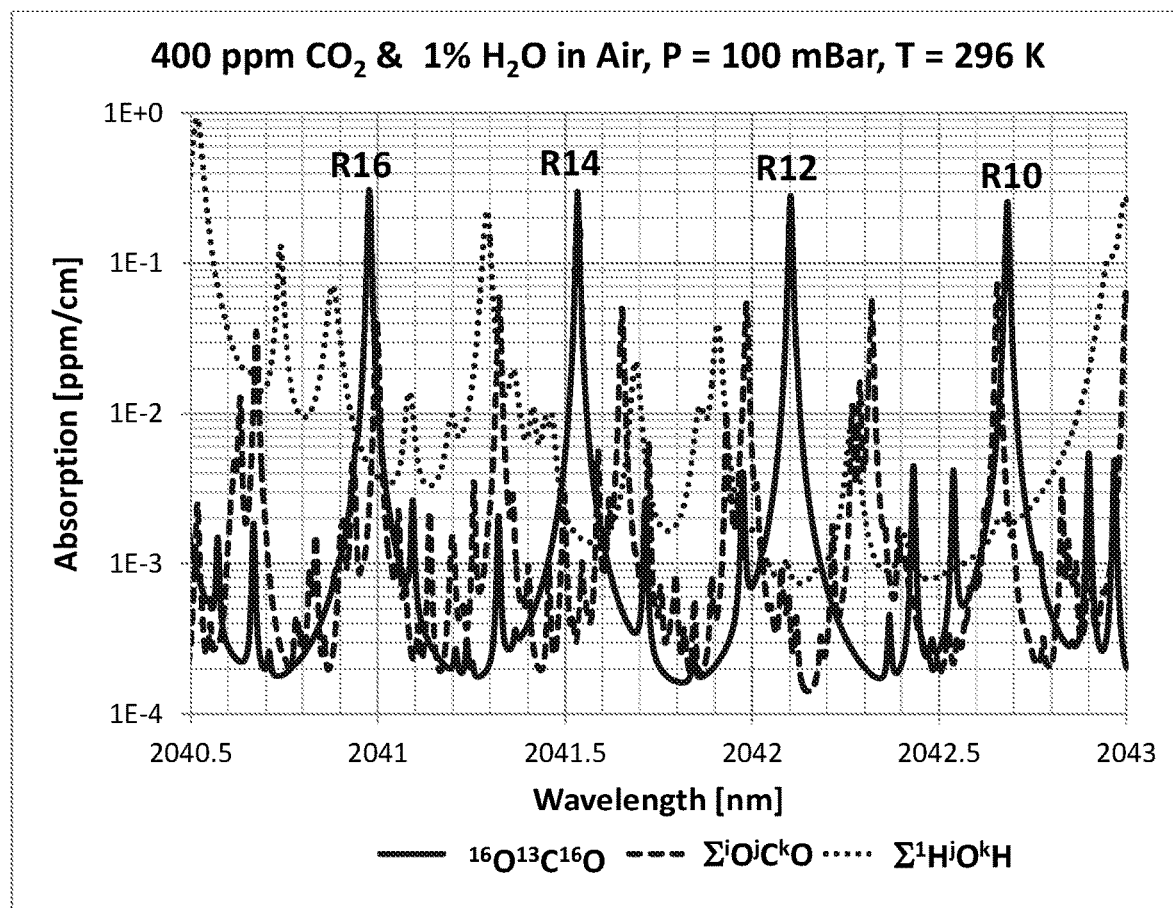
FIG. 17. Spectrum of the $^{13}C^{16}O_2$ isotopologue, the sum of spectra of all other isopologues of $CO_2$, and the sum of spectra of all isopologues of water from 2040.5 nm to 2043 nm at a pressure of 100 mBar and a temperature of 296 K. $R_x$ symbols show positions where the corresponding rotational-vibrational transitions, from one rotational level in the ground vibrational state to another rotational level in the vibrationally excited state $v_1+2v_2+v_3$ of $^{13}C^{16}O_2$ isotopologue, are located. The total concentration of carbon dioxide is 400 part per million. The total concentration of water is 1%.
Figure 18:
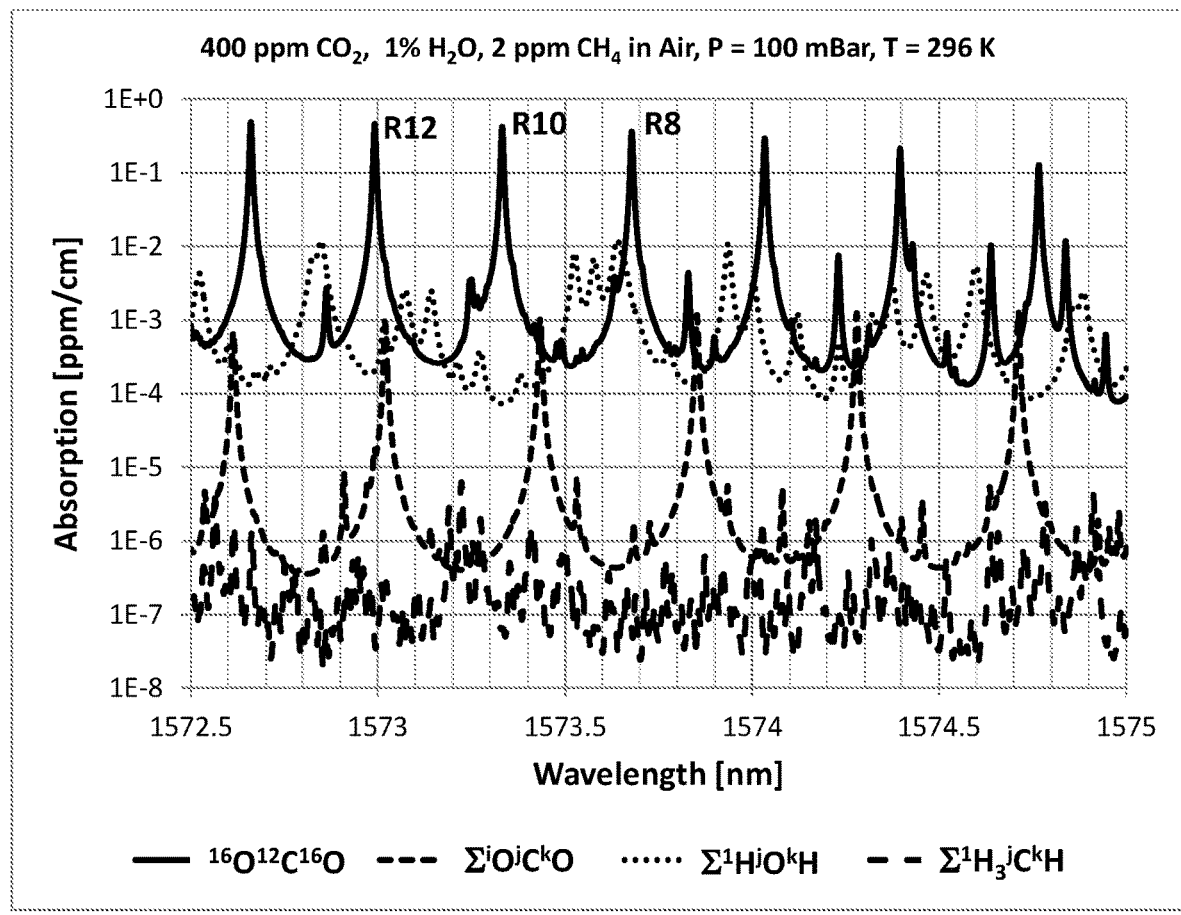
FIG. 18. Spectrum of the $^{12}C^{16}O_2$ isotopologue, the sum of spectra of all other isopologues of $CO_2$, the sum of spectra of all isopologues of water, and the sum of spectra of all isopologues of methane from 1572.5 nm to 1575 nm at a pressure of 100 mBar and a temperature of 296 K. $R_x$ symbols show positions where corresponding rotational-vibrational transitions from one rotational level in the ground vibrational state to another rotational level in the vibrationally excited state $2v_1+2v_2+v_3$ of $^{13}C^{16}O_2$ isotopologue are located. The total concentration of carbon dioxide is 400 part per million. The total concentration of water is 1%.

FIG. 17 and FIG. 18 show simulated absorptions spectra at two selected spectral regions. These figures show that by choosing rotational-vibrational lines which belong to different bands in different spectral regions, the instrument accuracy can be significantly improved: the analytical lines are not only relatively spectrally clean, but they also have close absorption coefficients and very close pressure broadening parameters and temperature dependencies. The first conditions permit to optimize the measurement method for both isotopologues. The last two conditions make these measurement less affected by both the pressure and temperature uncertainties.

According to another embodiment, a gas analyzer system is provided for measuring an isotopic ratio gas species. The system typically includes a resonant optical cavity having two or more mirrors and containing a gas having a chemical species to be measured, a laser optically coupled to the resonant optical cavity, and a detector system for measuring absorption of laser light by the gas in the cavity.

According to another embodiment, a gas analyzer system is provided for measuring an isotopic ratio gas species. The system typically includes a gas cell containing a gas to be measured, a laser optically coupled to the cell, and a detector system for measuring the laser light transmitted through the cell.

According to another embodiment, a gas analyzer system is provided for measuring an isotopic ratio of gas species. The system typically includes an optical cavity containing a gas having a chemical species to be measured, a laser optically coupled to the optical cavity, and a detector system for measuring absorption of laser light by the gas in the cavity. In certain aspects, the gas analyzer system utilizes the cavity ring-down spectroscopy method to measure absorption of the laser light by the gas in the cavity.

According to another embodiment, a gas analyzer system is provided for measuring an isotopic ratio of gas species. The system typically includes an optical cavity containing a gas having a chemical species to be measured, a laser optically coupled to the optical cavity, and a detector system for measuring absorption of laser light by the gas in the cavity. In certain aspects, the gas analyzer system utilizes the phase shift spectroscopy method to measure absorption of the laser light by the gas in the cavity.

According to another embodiment, a gas analyzer system is provided for measuring an isotopic ratio of gas species. The system typically includes an optical cavity containing a gas having a chemical species to be measured, a laser optically coupled to the optical cavity, and a detector system for measuring absorption of laser light by the gas in the cavity. In certain aspects, the gas analyzer system utilizes the cavity enhanced absorption spectroscopy method to measure absorption of the laser light by the gas in the cavity.

According to another embodiment, a gas analyzer system is provided for measuring an isotopic ratio of gas species. The system typically includes an optical cavity containing a gas having a chemical species to be measured, a laser optically coupled to the optical cavity, and a detector system for measuring absorption of laser light by the gas in the cavity. In certain aspects, the gas analyzer system utilizes the photoacoustic spectroscopy method to measure absorption of the laser light by the gas in the cavity.

According to another embodiment, a gas analyzer system is provided for measuring an isotopic ratio of gas species. The system typically includes an optical cavity containing a gas having a chemical species to be measured, a laser optically coupled to the optical cavity, and a detector system for measuring absorption of laser light by the gas in the cavity. In certain aspects, the gas analyzer system utilizes the tunable diode lasers spectroscopy method to measure absorption of the laser light by the gas in the cavity.

According to another embodiment, a gas analyzer system is provided for measuring an isotopic ratio of gas species. The system typically includes an optical cavity containing a gas having a chemical species to be measured, a laser optically coupled to the optical cavity, and a detector system for measuring absorption of laser light by the gas in the cavity. In certain aspects, the gas analyzer system also includes a temperature sensor for measuring the temperature of the gas in the cavity, and a pressure sensor for measuring the pressure of the gas in the cavity. In certain aspects, the detector system includes one of a photo-detector configured to measure an intensity of the intra-cavity light or both a photo-acoustic sensor configured to measure photo-acoustic waves generated in the cavity and a photo-detector configured to measure an intensity of the intra-cavity light.

According to yet another embodiment, a gas analyzer system is provided for measuring an isotopic ratio gas species. The system typically includes an optical cavity containing a gas having a chemical species to be measured, a laser optically coupled to the optical cavity, and a detector system for measuring the absorption of laser light by the gas in the cavity. In certain aspects, the gas analyzer system also includes a control element configured to control temperature of the gas in the optical cavity and a pressure control element configured to control pressure of the gas in the optical cavity.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein.

The invention claimed is:

1. A gas analyzer system for measuring an isotopic composition of a gaseous chemical species by an optical absorption spectroscopy method, the system comprises: a multipass cell containing a gas mixture with the chemical species to be measured; a laser configured to produce a laser beam directed to the multipass cell; a detector system for measuring a laser light transmitted through multipass cell; and an intelligence module comprising a processor adapted to determine an isotopic composition of the gaseous chemical species, wherein rotational-vibrational spectra of the chemical species are measured at least within two non-overlapping spectral intervals separated by a minimum of 50 nm and selected in such a way that a first rotational-vibrational line of a first rotational-vibrational band of a first isotopologue is located in a first spectral interval, and a second rotational-vibrational line of a second rotational-vibrational band of a second isotopologue is located in a second spectral interval, and the second rotational-vibrational band is different from the first rotational-vibrational band.

2. The system of claim 1, wherein the spectral intervals selected in such a way that in the first spectral interval an absorption spectrum of the first isotopologue exceeds somewhere the sum of absorption spectra of all other isotopologues of the chemical species weighted by mole-fraction abundance figures, and in the second spectral interval an absorption spectrum of the second isotopologue exceeds somewhere the sum of absorption spectra of all other isotopologues of the chemical species weighted by mole-fraction abundance figures.

3. The system of claim 1, wherein a ratio of an air-broadened half-width $\gamma_{air1}$ of the first line to an air-broadened half-width $\gamma_{air2}$ of the second line is between 0.5 and 2.

4. The system of claim 1, wherein a ratio of a self-broadened half-width $\gamma_{self1}$ of the first line to a self-broadened half-width $\gamma_{self2}$ the second line is between 0.5 and 2.

5. The system of claim 1, wherein a ratio of the temperature dependence coefficient $dS_1/S_1 dT$ of the first line to the temperature dependence coefficient $dS_2/S_2 dT$ of the second line is between 0.5 and 2.

6. The system of claim 1, wherein an absolute value of the temperature dependence coefficient $|dS_1/S_1 dT|$ of the first line and an absolute value of the temperature dependence coefficient $|dS_2/S_2 dT|$ of the second line is less than 0.004 $K^{-1}$.

7. The system of claim 1, wherein a third rotational-vibrational line of one of the isotopologues of the gaseous chemical species is measured, and the intelligence module, by comparing a line intensity of the third line with the line intensity of either one of the first two lines, evaluates a temperature of the gas in the multipass cell.

8. The system of claim 1, wherein a spectral profile of a rotational-vibrational line is measured and the intelligence module based on the measured spectral profile evaluates the pressure of the gas in the multipass cell.

9. The system of claim 1, further comprising a temperature sensor for measuring the temperature of the multipass cell, a pressure sensor for measuring the pressure of the gas in the multipass cell, a temperature control element configured to control the temperature of the multipass cell, and a pressure control element configured to control the pressure of the gas in the multipass cell.

10. The system of claim 1, wherein the multipass cell is disposed in a housing that provides an airtight seal for the multipass cell, and wherein the temperature and the pressure of a gas in the housing are actively controlled.

11. The system of claim 1, wherein a single mode optical fiber is used to deliver the laser beam directed to the multipass cell and a single mode optical fiber is used to deliver the laser light transmitted through multipass cell to detector system.

12. The system of claim 1, wherein the system measures a concentration of a gaseous chemical species different from the gaseous chemical species of which the isotopic composition is measured.

13. The system of claim 1, further comprising a gas analyzer for measuring a concentration of a gaseous chemical species different from the chemical species of which the isotopic composition is measured.

14. The system of claim 1, further comprising a gas multiplexer for delivering different gases to the multipass cell.

15. The system of claim 1, the system having at least two multipass cells in fluid communication with each other, wherein a first multipass cell is adapted to measure absorption spectra in the first spectral interval and a second multipass cell is adapted to measure absorption spectra in the second spectral interval.

* * * * *